(12) United States Patent
Turner et al.

(10) Patent No.: US 7,565,207 B2
(45) Date of Patent: Jul. 21, 2009

(54) APPARATUS FOR CREATING HYPERTHERMIA IN TISSUE

(75) Inventors: Paul F. Turner, Bountiful, UT (US); Mark Hagmann, Salt Lake City, UT (US)

(73) Assignee: BSD Medical Corporation, Salt Lake City, UT (US)

( * ) Notice: Subject to any disclaimer, the term of this patent is extended or adjusted under 35 U.S.C. 154(b) by 699 days.

(21) Appl. No.: 11/286,104

(22) Filed: Nov. 22, 2005

(65) Prior Publication Data

US 2007/0118193 A1   May 24, 2007

(51) Int. Cl.
*A61N 5/00* (2006.01)

(52) U.S. Cl. .................. 607/100; 607/101; 607/156

(58) Field of Classification Search ......... 607/100–102, 607/154, 156; 600/10, 411, 549
See application file for complete search history.

(56) References Cited

U.S. PATENT DOCUMENTS

| | | | |
|---|---|---|---|
| 2,533,900 A | 12/1950 | Shanklin | |
| 3,095,880 A | 7/1963 | Haagensen | |
| 3,594,802 A | 7/1971 | Koob | |
| 4,397,313 A | 8/1983 | Vaguine | |
| 4,434,341 A | 2/1984 | Busby | |
| 4,462,412 A | 7/1984 | Turner | |
| 4,586,516 A | 5/1986 | Turner | |
| 4,589,423 A | 5/1986 | Turner | |
| 4,612,940 A | 9/1986 | Kasevich et al. | |
| 4,633,875 A | 1/1987 | Turner | |
| 4,638,813 A | 1/1987 | Turner | |
| 4,672,980 A | 6/1987 | Turner | |
| 4,785,829 A * | 11/1988 | Convert et al. | 607/101 |
| 4,798,215 A | 1/1989 | Turner | |
| 5,026,959 A * | 6/1991 | Ito et al. | 219/690 |
| 5,097,844 A | 3/1992 | Turner | |
| 5,101,836 A | 4/1992 | Lee | |
| 5,251,645 A | 10/1993 | Fenn | |
| 5,284,144 A | 2/1994 | Delannoy et al. | |
| 5,441,532 A | 8/1995 | Fenn | |
| 5,492,122 A | 2/1996 | Button et al. | |

(Continued)

FOREIGN PATENT DOCUMENTS

DE   2420883   11/1975

(Continued)

*Primary Examiner*—Lee S Cohen
*Assistant Examiner*—Kaitlyn E Helling
(74) *Attorney, Agent, or Firm*—Thorpe North & Western LLP

(57) ABSTRACT

A system and corresponding method for creating hyperthermia in a selected position in target tissue using the application of electromagnetic radiation (EMR) in the HF, VHF and UHF microwave region and phased array steering includes an array of applicators and a single channel EMR radiation energy source coupled to at least one of the applicators of the array. A variable reflective termination device is coupled to at least one of the applicators so that a user can vary the energy radiated from the coupled applicator to steer the heating region in the target to a desired position in the target. Several different applicator arrays are suitable for use with the system, and comprise generally cylindrical annuli which emit radiation toward a central axis. Parasitic applicators with variable reflective termination devices can be used in the applicator array along with at least one applicator directly coupled to the energy source.

21 Claims, 8 Drawing Sheets

U.S. PATENT DOCUMENTS

| | | |
|---|---|---|
| 5,501,655 A | 3/1996 | Rolt et al. |
| 5,540,737 A | 7/1996 | Fenn |
| 5,810,888 A | 9/1998 | Fenn |
| 5,895,356 A | 4/1999 | Andrus et al. |
| 6,200,598 B1 | 3/2001 | Needham |
| 6,470,217 B1 | 10/2002 | Fenn et al. |
| 6,592,847 B1 | 7/2003 | Weissleder et al. |
| 6,904,323 B2 | 6/2005 | Samulski |
| 6,917,338 B2 | 7/2005 | Bergervoet et al. |
| 2002/0193849 A1 | 12/2002 | Fenn et al. |
| 2003/0004454 A1 | 1/2003 | Fenn et al. |
| 2008/0228063 A1 * | 9/2008 | Turner et al. ................ 600/411 |

FOREIGN PATENT DOCUMENTS

FR        1233947        10/1960

* cited by examiner

APPARATUS FOR CREATING HYPERTHERMIA IN TISSUE

BACKGROUND OF THE INVENTION

1. Field

The present invention relates generally to systems and apparatus for irradiating targets with electromagnetic radiation, and more specifically to systems having annular-type or various sectored applicators and associated control systems for controlling application of radiation to targets through phased array power steering.

2. State of the Art

Current systems for applying electromagnetic radiation (EMR) to targets, such as living bodies and biological tissue, and controlling the position of a region of heating within the target through phased array power steering are provided with a plurality of electromagnetic applicators powered by multi-channel EMR systems where different applicators are each provided with electronically controlled power of electronically controlled phase by different power channels of the EMR system. This creates a desired phased array heat pattern steering capability. Such an approach results in high system complexity and cost in order to provide such phased array heat pattern steering.

Several types of therapeutic treatments for cancer in humans are in current, common use. These treatments include surgery, X-rays, radiation from radioactive sources, and chemotherapy. These treatments are often combined in various ways to enhance treatment effectiveness.

Although such conventional treatment techniques have been successful in treating cancer in many patients and in prolonging the lives of many other patients, they are frequently ineffective against many types of cancer and often have severe adverse side effects at the necessary treatment levels. Protracted treatment of cancer patients by X-rays or chemotherapy, as an illustration, tends to eventually destroy or inhibit the patients' natural immunological systems to an extent that many patients eventually succumb to common infectious diseases, such as influenza or pneumonia, which otherwise probably would not be fatal. Also, many patients having advanced stages of cancer or complications may become too weak to withstand the trauma of surgical or other cancer treatments; hence, the treatments cannot be undertaken or must be discontinued.

Due both to the prevalence and the typically severe consequences of human cancer, as well as frequent ineffectiveness of current treatments such as those mentioned above, medical researchers are continually experimenting in an attempt to discover and develop improved or alternative cancer treatment methods with their associated treatment apparatus.

Hyperthermia, the generation of artificially elevated body temperatures, has recently been given serious scientific consideration as an alternative cancer treatment. Much research has been conducted into the effectiveness of hyperthermia alone or in combination with other treatment methods. This research is important in that hyperthermia techniques appear to have the potential for being extremely effective in the treatment of many or most types of human cancers, without the often severely adverse side effects associated with current cancer treatments. Hyperthermia is sometimes called thermal therapy indicating the raising of the temperature of a region of the body.

Researchers into hyperthermia treatment of cancer have commonly reported that many types of malignant growths in humans can be thermally destroyed, usually with no serious adverse side effects, by heating the malignancies to temperatures slightly below that injurious to most normal, healthy cells. Furthermore, many types of malignant cell masses have reportedly been found to have substantially lower heat transfer to lessen the ability to dissipate heat, presumably due to poorer vascularity and reduced blood flow characteristics. Consequently, these types of growths appear capable of preferential hyperthermia treatment. Poorly vascular malignant growths can reportedly be heated to temperatures several degrees higher than the temperature reached by the immediately surrounding healthy tissue. This promises to enable hyperthermic treatment of those types of malignant growths which are no more thermally sensitive than normal tissue without destruction of normal cells, and additionally to enable higher temperature, shorter hyperthermia treatment times of more thermally sensitive types of malignancies which exhibit poor vascularity, usually an advantage for important medical reasons.

In this regard, researchers have commonly reported that as a consequence of these thermal characteristics of most malignant growths and the thermal sensitivity of normal body cells, hyperthermia temperatures for treatment of human cancer should be carefully limited within a relatively narrow effective and safe temperature range. Hyperthermia is generally provided by temperatures over 40 degrees C. (104 degrees F.). Hyperthermia has historically included temperatures well above 60 degrees C., but in recent years has generally been considered to include temperatures as high as 45 degrees C. (113 degrees F.). However, there may be portions of a cancerous tumor that will exceed this level, the intent is to attempt to get as much of the tumor region above the 40 degree C. region as possible.

At treatment temperatures above the approximate 45 degrees C. (113 degrees F.), thermal damage to most types of normal cells is routinely observed if the time duration exceeds 30 to 60 minutes; thus, great care must be taken not to exceed these temperatures in healthy tissue for a prolonged period of time. Exposure duration at any elevated temperature is, of course, an important factor in establishing the extent of thermal damage to healthy tissue. However, if large or critical regions of the human body are heated into, or above, the 45 degree C. range for even relatively short times, normal tissue injury may be expected to result.

Historically, late in the last century alternating electric currents at frequencies above about 10 KHz were found to penetrate and cause heating in biological tissue. As a result, high frequency electric currents, usually in the megahertz frequency range, have since been widely used for therapeutic treatment of such common bodily disorders as infected tissue and muscle injuries. Early in this century, the name "diathermy" was given to this EMR tissue heating technique, and several discrete EMR frequencies in the megahertz range have subsequently been allocated specifically for diathermy use in this country by the Federal Communications Commission (FCC).

Extensive articles and reports have been written on the use of the phased array principle to provide hyperthermia heat pattern steering, and several patents have been issued covering use of phased arrays. All have relied upon the use of electronic phase and power steering to provide heat pattern steering control. This results in relatively complicated equipment configurations with multiple channel controls of power and phase. Such configurations can be difficult for routine clinical professionals to learn and utilize in the clinic. The simpler the clinical controls are in such a treatment system, the easier the operation of the system and potentially the greater the reliability. Simplicity of such designs may further lead to fewer system failures due to component failures. The utilization of standardized heating regions provided by standard energy steering configurations is expected to provide improved adaptation for clinical use.

The BSD-2000 system produced by BSD Medical Corporation, Salt Lake City, Utah, utilizes multi-channel phased array systems that control frequency, radiated power, and relative phase. Each channel has electronic controls of power and phase and is connected to different antennas. This allows electronic steering of the heating pattern, but at high cost and complexity. Such high cost can be cost prohibitive for routine clinical use. The ability to do heat pattern steering permits energy to be focused and directed more selectively to the target tumor region. In order to provide sufficient heat energy penetration, a lower frequency must be selected. This is because the penetration attenuation of human tissue increases at higher frequencies. As frequency is lowered however, the heating focus diameter increases. Thus, the proper frequency is needed to provide the optimum depth within acceptable heating pattern size limits. In general, hyperthermia is best applied when tumor target tissues around the diseased area is also heated. This provides preheating of in flowing blood and reduces thermal conduction from the perimeter of the tumor to draw heat out of the tumor perimeter. The BSD-2000 system has been investigated since 1988. The novel use of such phased arrays systems has proven to be useful and beneficial in treating patients with various forms of cancers, even in Phase III clinical trials. However, the use of complex and expensive multi-channel amplifier systems to provide multiple EMR synchronous phase energy channels that have phase control to steer the heating region in the body has excessive complexity for routine clinical use in some treatment centers.

There is a need for EMR applicator apparatus, and corresponding methods for EMR irradiation, which provide simplified heat pattern steering of EMR heating in a target, such as a target of biological tissue in a living body or tissue simulating matter.

SUMMARY OF THE INVENTION

According to the present invention, a simplified hyperthermia system utilizing an array of electromagnetic radiation applicators utilizes variable reflective termination devices coupled to the applicators to control the phase of the EMR power applied to the individual applicators to steer and control the position of the system heating region in the target. The EMR power can be supplied to the applicators by a single EMR power source and the phase of the EMR radiation directed toward the target by each of the individual applicators is controlled by the variable reflective termination devices. The state of a variable reflective termination device, e.g., whether the termination presents an open circuit or a short circuit, can be easily varied by a user of the system to control the phase of reflected EMR power at the connection to the applicator, which controls the phase of the radiation from the particular applicator. By controlling the phase of the radiation from each applicator in this manner, the position of the heated region in the target can be steered and controlled without the need for a separate power channel in the EMR power source for each applicator. A single EMR energy source with a passive power splitter can be used to supply EMR energy of approximately equal power and phase to all applicators through the power splitter and the phase of energy radiated by each individual applicator is easily controlled by the variable reflective termination device.

While it is currently preferred that the EMR power source be coupled to all applicators in the array, some of the applicators in the array can be parasitic applicators, i.e., not directly coupled to the EMR power source. These non-active, parasitic applicators will re-radiate EMR energy with the phase of the re-radiated energy dependent upon the termination of the applicator. The termination can be made adjustable by connection of a variable reflective termination device coupled to the applicator.

While it is currently preferred that variable reflective termination devices be coupled to each applicator in the array, depending upon the adjustability of the heating region positioning required or desired, it is not necessary to connect a variable reflective termination device to each applicator. As a minimum, it is only necessary that one applicator be coupled to the EMR power source and that only one applicator be connected to a variable reflective termination device. If only one applicator is coupled directly to the power source, the variable reflective termination device will need to be coupled to a different applicator to provide the system with any steering capability.

The applicator array of the invention will usually be formed of a plurality of individual applicators for directing EMR energy toward the target. The EMR power source is coupled to supply EMR energy to one or more of the individual applicators, which are the primary radiators. The power source is controlled to control the amplitude and phase of energy supplied by the power source to the primary radiators. The power source can be a high output power, single channel power source that uses a passive power splitter to activate the primary radiators with EMR power of approximately equal power and phase. Preferably all applicators are primary radiators coupled to the power source through the power splitter, although some of the applicators can be pasasitic non-active, passive radiators that re-radiate EMR energy. The power and phase of this re-radiated energy is determined by the terminations of the parasitic applicators. Variable reflective termination devices preferably provide the termination of the passive applicators and the state of the variable reflective termination devices determine the phase of the re-radiated energy and the resulting heating pattern of the applicator array.

In a currently preferred embodiment, four primary radiators are positioned around a target to be radiated. All radiators are primary radiators coupled to a single channel, high power EMR power source through a passive power splitter that splits the EMR power from the source into four separate channels of approximately equal power and phase. The applicators each include at least one antenna and each have a central energy supply connection point. Each applicator is coupled to the power splitter by a cable of predetermined length extending from the power splitter to the applicator central energy supply connection point. Each applicator central energy supply connection point is thus provided with approximately equal power of equal phase through the power splitter from the EMR power source. Also each applicator is connected to a variable reflective termination device through a cable of predetermined length also connected to the central energy supply connection point. The length of the cable between the central energy supply connection point and the variable reflective termination device and the state of the variable reflective termination device determine the apparent state of the central energy supply connection point to incoming EMR power and determines the phase of the EMR energy radiated from the antennas of the applicator. This arrangement provides offset heat pattern steering toward the surface of the body while preserving significant deep heating energy penetration. It provides control to direct the region of heating away from a centered region in the target to eight offset positions rotated forty-five degree around the target from one another. The target will usually be a human patient or tissue sample to be heated which is positioned in a housing. The applicators are preferably arranged around the housing to encircle the target placed in the housing. A dielectric fluid having an impedance approximately equivalent to an applicator impedance at the predetermined frequency of the EMR radiation being used in the system fills the housing around the target. The housing will generally include a bolus inside the housing around the target to contain the fluid.

Rather than four separate applicators in the system described, a single applicator formed by two concentric metallic cylinders surrounding the target can be used and can be configured to have the same EMR energy steering as described above. The steering is provided by placing variable reflective termination devices between the two concentric rings at spaced intervals around the rings so that the devices can provide an equivalent short circuit termination between the two metal rings to steer the energy away from the short. This short circuit configuration can be achieved by joining common ends of the dipoles or filling the spaces partially or totally between the adjacent dipole ends.

The system can utilize different types of EMR applicators to heat the target. The individual applicators may be, for example, horn type radiators, patch radiators, dipole antennae, folded dipoles, monopoles, waveguides, two concentric metal cylinders that surround the target to form a single dipole, etc. It is preferred that these antenna sources are linearly polarized for the greatest enhancement of the heating in the overlapping wave targeted region.

The system of the present invention provides lower cost and complexity for phased array control of heating patterns in predictable steering positions in a target through the use of variable reflective termination devices to select and control the reflective terminations of at least one of the applicators in an array. Such variable reflective termination devices can include open circuit and short circuit terminations, variable cable lengths, or similar devices. These devices are also used to create the same effects with parasitic antennas or combinations of primary and parasitic antennas for phase steering of a phased array of antennas. The system of the invention provides a simplified annular applicator apparatus for EMR heating for any required purpose, such as medical hyperthermic treatment of cancer or of other medical uses or research.

THE DRAWINGS

In the accompanying drawings, which show the best mode presently contemplated for carrying out the invention:

Figure 1:
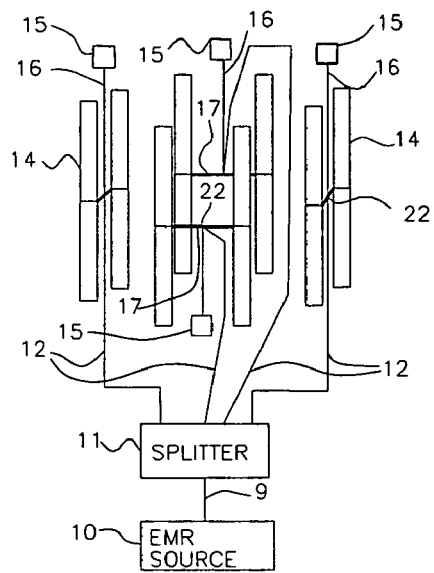
FIG. 1 is a schematic diagram of a system of the invention for creating hyperthermia in a target using active energy at feed points of an antenna applicator array with variable phase terminations used to alter the resultant phase radiated from each antenna group.
Figure 5:
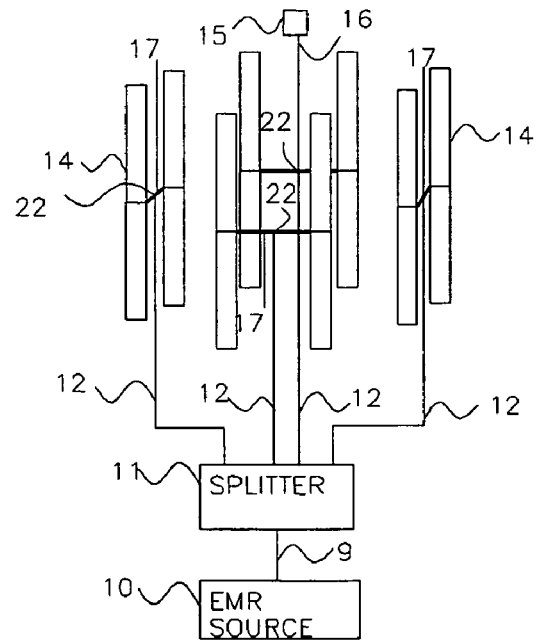

FIG. 5 is a diagram similar to that of FIG. 1, but showing a phased array system with limited phase steering capability with a variable reflective termination device coupled to one of the applicators at its feed point so the phase of the termination can be altered to steer the resulting heating pattern created by the system in a body either toward or away from the applicator with the termination device.

Figure 6:
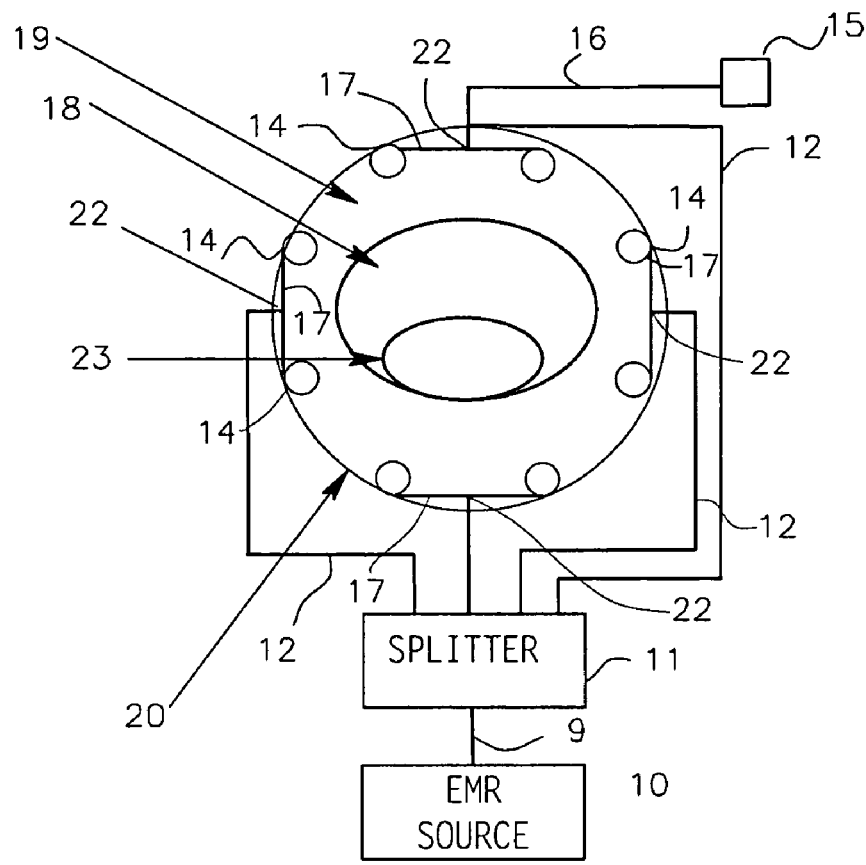

FIG. 6 is a schematic top view of the system of FIG. 5 showing an elliptical target body centrally located inside a cylindrical housing and antenna array and showing the steered heated area displaced in the body away from the applicator with the termination device.

Figure 7:
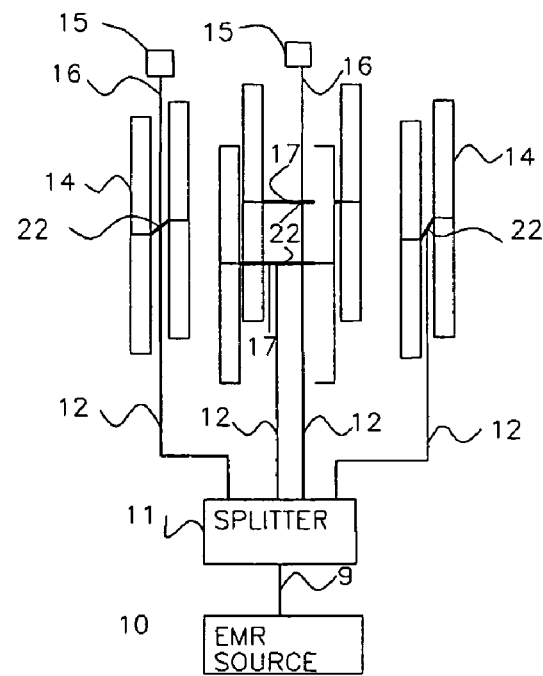

FIG. 7 is a diagram similar to that of FIG. 1, but showing a phased array system with limited phase steering capability with a variable reflective termination device coupled to two adjacent applicators at their feed points so the phase of the termination can be altered to steer the resulting heating pattern created by the system in a body either toward or away from the applicators with the termination devices.

Figure 8:
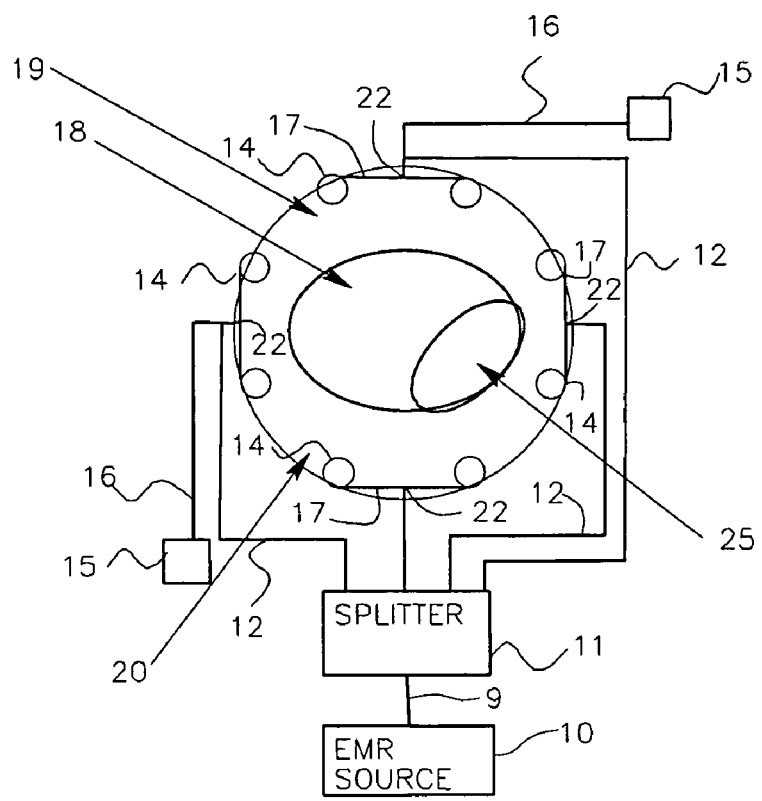

FIG. 8 is a schematic top view of the system of FIG. 7 showing an elliptical target body centrally located inside a cylindrical housing and antenna array and showing the steered heated area displaced in the body away from the two adjacent applicators with the termination devices.

Figure 9:
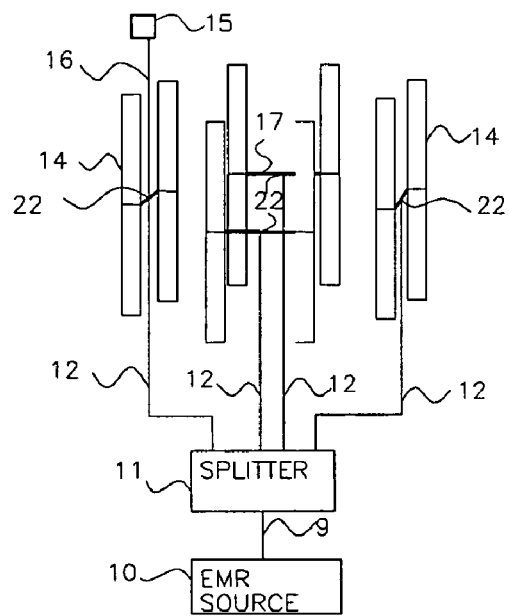

FIG. 9 is a diagram similar to that of FIG. 5, showing a similar phased array system with limited phase steering capability with a variable reflective termination device coupled to a different one of the applicators at its feed point so the phase of the termination can be altered to steer the resulting heating pattern created by the system in a body either toward or away from the applicator with the termination device.

Figure 10:
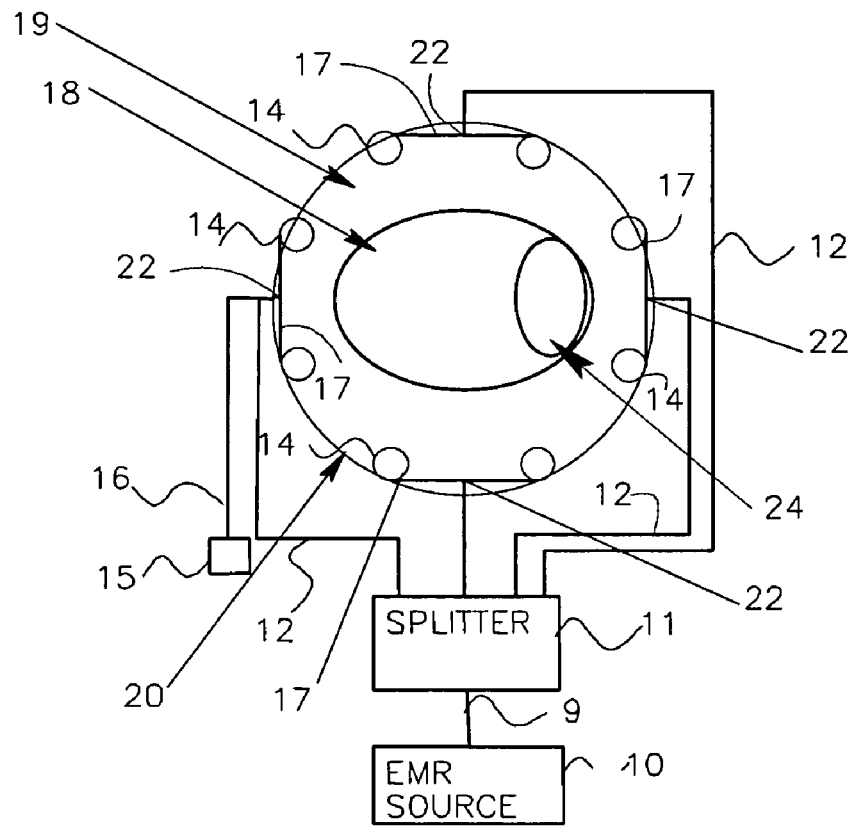

FIG. 10 is a schematic top view of the system of FIG. 9 showing an elliptical target body centrally located inside a cylindrical housing and antenna array and showing the steered heated area displaced in the body away from the applicator with the termination device.

Figure 11:
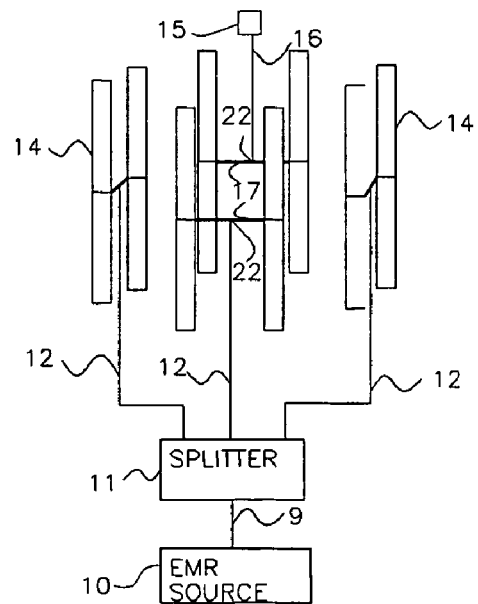

FIG. 11 is a diagram similar to that of FIG. 5, showing a similar phased array system with limited phase steering capability with one applicator having only a variable reflective termination device connected at its feed point with no connection to the EMR energy source at its feed point so the phase of the termination can be altered to steer the resulting heating pattern created by the system in a body either toward or away from the applicator with the termination device.

Figure 12:
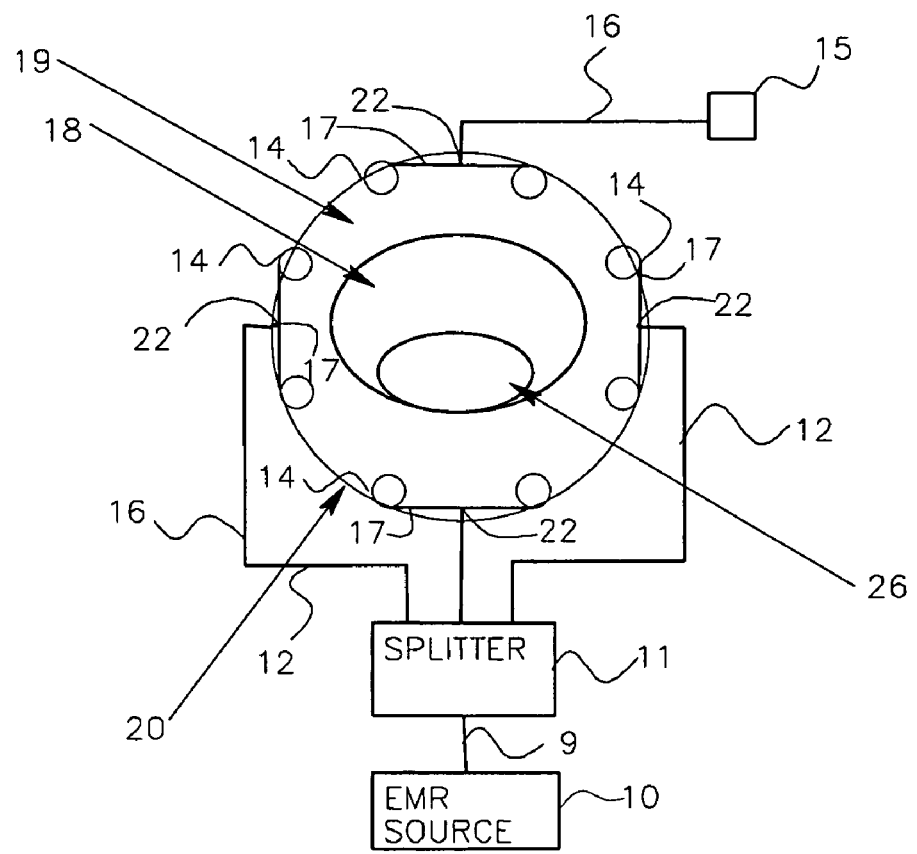

FIG. 12 is a schematic top view of the system of FIG. 1 showing an elliptical target body centrally located inside a cylindrical housing and antenna array and showing the steered heated area displaced in the body away from the applicator with the termination device.

Figure 13:
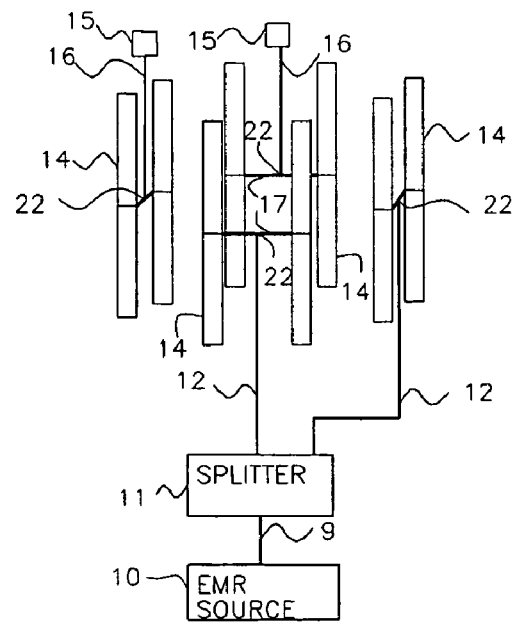

FIG. 13 is a diagram similar to that of FIG. 7, but showing a phased array system with limited phase steering capability with two adjacent applicators having only a variable reflective termination device connected at their feed points with no connection to the EMR energy source at their feed points so the phase of the terminations can be altered to steer the resulting heating pattern created by the system in a body either toward or away from the applicators with the termination devices.

Figure 14:
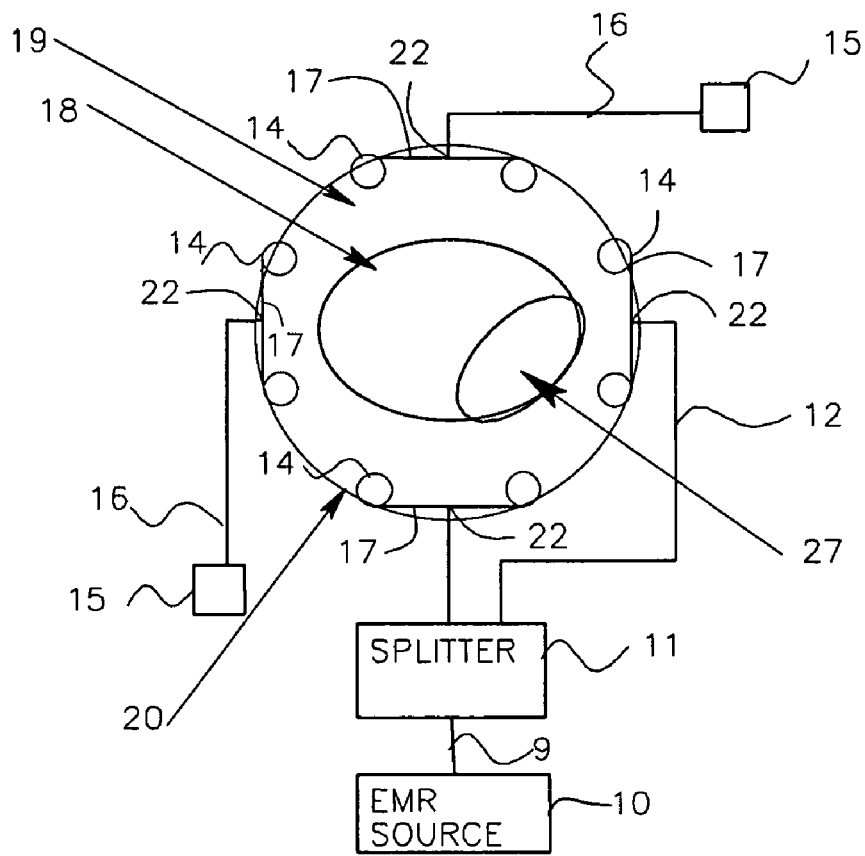

FIG. 14 is a schematic top view of the system of FIG. 13 showing an elliptical target body centrally located inside a cylindrical housing and antenna array and showing the steered heated area displaced in the body away from the two adjacent applicators with the termination devices.

Figure 15:
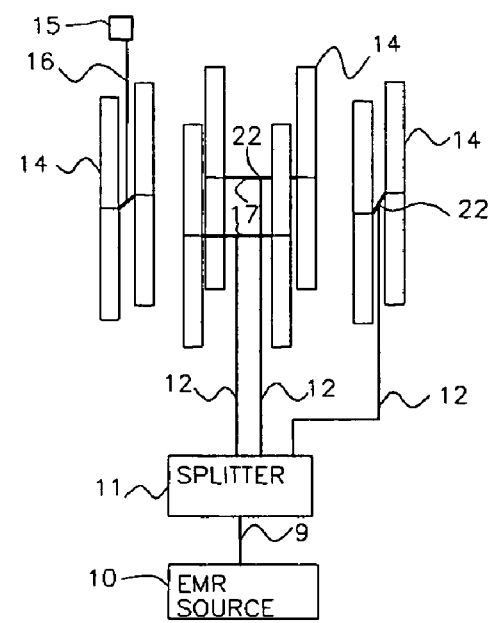

FIG. 15 is a diagram similar to that of FIG. 11, showing a similar phased array system with limited phase steering capability with a different one of the applicators having only a variable reflective termination device connected at its feed point with no connection to the EMR energy source at its feed point so the phase of the termination can be altered to steer the resulting heating pattern created by the system in a body either toward or away from the applicator with the termination device.

Figure 16:
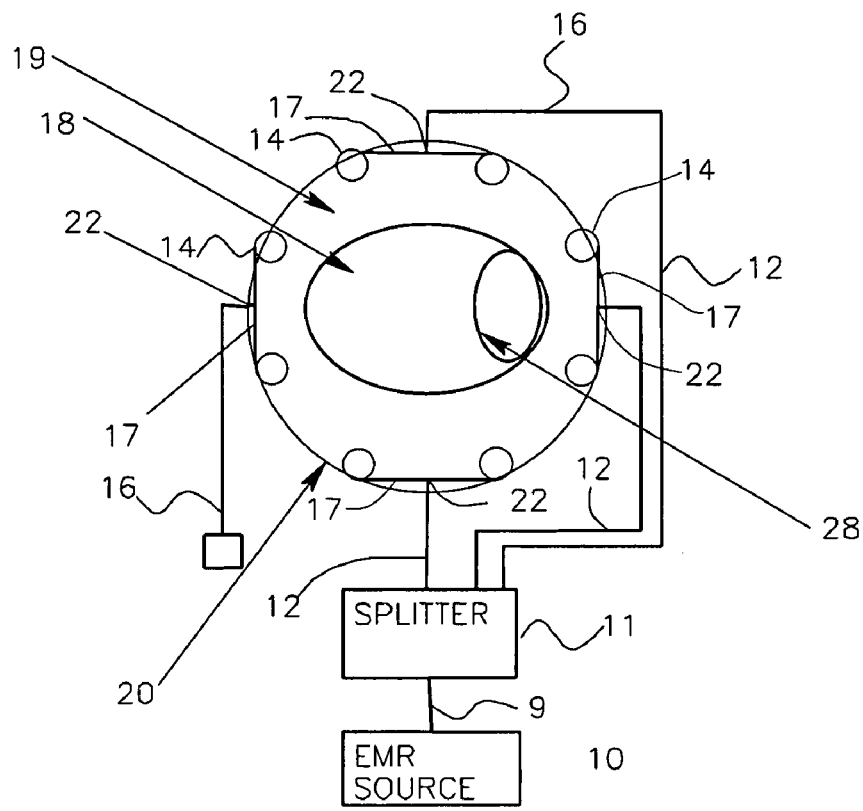

FIG. 16 is a schematic top view of the system of FIG. 15 showing an elliptical target body centrally located inside a cylindrical housing and antenna array and showing the steered heated area displaced in the body away from the applicator with the termination device.

Figure 2:
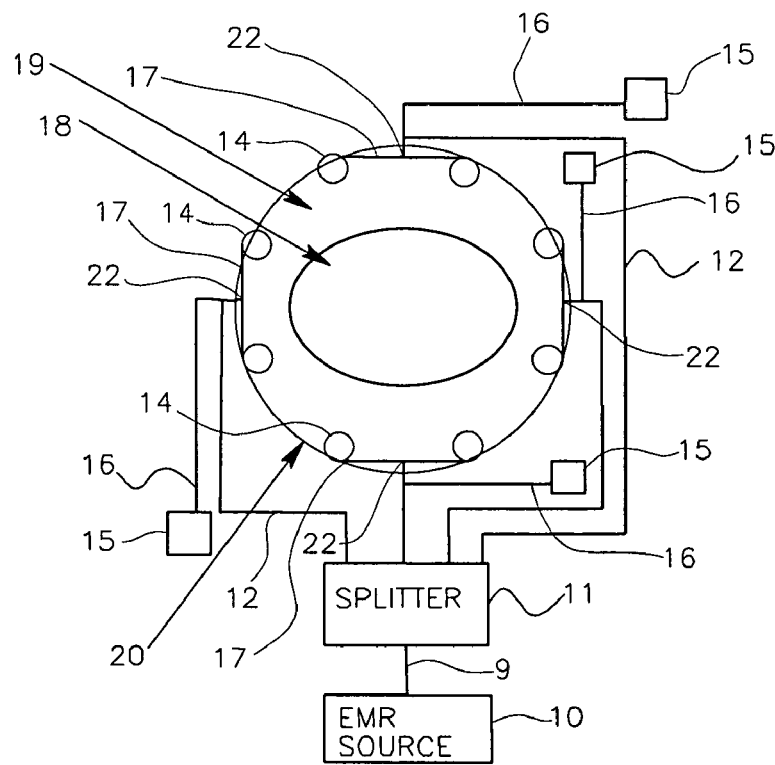
FIG. 2 is a schematic top view of the system of FIG. 1 showing an elliptical target body centrally located inside a cylindrical housing and antenna array.
Figure 17:
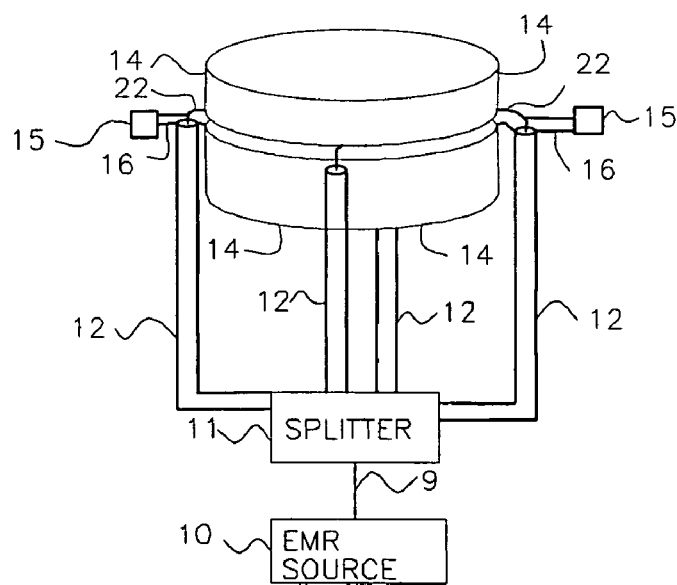

FIG. 17 is a schematic diagram of a system of the invention with full steering capability similar to the system shown in FIG. 1 but showing an applicator formed of two concentric metal cylinders that surround the target forming a single dipole with localized EMR signal feed connections between the cylinders at four points spaced at ninety degree intervals around the cylinders and with variable reflective termination devices coupled to each feed point between the two cylinders to provide steering similar to that provided by the system of FIGS. 1 and 2.

DETAILED DESCRIPTION OF THE ILLUSTRATED EMBODIMENTS

The apparatus of the invention, as shown in FIG. 1, includes an electromagnetic radiation (EMR) energy source 10 connected to a power splitter 11 that splits the EMR energy from source 10 into a plurality of outputs each connected to one of a plurality of applicators each including one or more antennas 14 connected by cables 17 and having central energy supply connection points 22. The antennas 14 radiate the EMR energy into a body 19, FIG. 2, positioned inside a dielectric shell or housing 20 for heating a target area in the body 19.

The EMR energy source 10 generally provides EMR energy in a frequency from 40 to 1000 MHz. For heating in human adult torso regions, the preferred frequencies are from 40 to 200 MHz. This is because the penetration losses and the localized heating capability at these frequencies provide for selective targeting and steering in useful regions with adequate penetration to heat deeply. The power splitter 11 is a passive power splitter configured without internal loss generally for more efficient operation. This then provides energy that is directed to an antenna group to be partially or totally reflected with various phases to alter the location of the phase focusing in the body. The EMR source 10 is connected to the power splitter 11 using a coaxial transmission line 9. The power received by splitter 11 is divided between the output coaxial ports, here shown as four coaxial output ports, based upon the impedance presented to the passive power splitter by each of the output coaxial cables 12. The cables 12 are used to connect the power from the power splitter 11 to the central energy supply connection points or feed points 22 of each applicator, here shown as four applicators, that are each comprised of single or multiple antennas 14 connected by cables 17. At these feed points 22, there are additional coaxial cables 16 that are used to attach to variable reflective termination devices 15. These variable reflective termination devices control the effective termination seen at the central energy supply connection points 22.

The variable reflective termination devices 15 can be, for example, coaxial shorts or coaxial opens where changing a termination from an electrical short circuit to an electrical open circuit will alter the reflected phase by one hundred eighty degrees to provide differing phase steering effects. If the effective termination 15 for example is a short circuit and is connected by a cable 16 that is one quarter wave length long, the effect of that short circuit appears as an open circuit at the feed point 22 and provides for a central focal region of the heating pattern. This same result will occur if cable 16 is one quarter, three quarters, one and one quarter, one and three quarters, etc. in length. However, when this variable termination is changed to an open circuit at the end of the quarter wave length cable 16, the resulting heating pattern is steered away from that applicator or antenna region as the effective termination at the feed point is that of a short circuit. In this case, the energy provided to the feed point 22 from this effective short is reflected back through the coaxial cable 12 to the power splitter 11. When the reflective energy arrives at the power splitter 11, the cable length 12 should be chosen so that the reflected phase from the variable termination 22 approximately appears as an open circuit so that it does not alter the phase or the impedance matching of other splitter ports, but just reflects its power back to the splitter 11 to be redirected out of the other splitter ports. If this reflected phase from the feed point termination 15 that places a short at the feed point 22 would appear as a short circuit at the junction internal to the splitter 11, then the splitter 11 would reflect too much power back to the EMR source 10. Therefore, the length of the cables 12 should be a quarter wave length long or an odd multiplier of a quarter wave length (¼, ¾, ⅝, ⅞, 9/4, etc.). This will assure that a short circuit at the feed point 22 will appear as an open circuit at the splitter 12. When the termination 15 in this example places the equivalent of an open circuit at the feed point 22, then the impedance from the antenna group associated with that channel will reflect a termination impedance of the radiating antennas (typically 50 ohms so the coaxial cable line is impedance is matched). This reflection that appears as an open circuit at 11 from an effective short termination at the feed point 22 will cause a partial mismatch of impedance in the splitter 11, but this will not significantly alter the impedance match provided to the EMR source 10 for a power splitter 11 having four or more output cables 12.

If the termination example is changed so that cables 16 are an integral number of half wavelengths, then the termination to provide an effective short at the feed point 22 would need to be a short circuit. This is because a short circuit appears as a short circuit impedance at a half wavelength from the short termination.

FIG. 2 is a top view of the arrangement of FIG. 1 that shows a diagrammatic cross-sectional view of the elliptical section 18 representing the human body as a target for radiation heating. The body 18 is surrounded by a housing or high dielectric shell 20 with the applicators spaced around the shell or housing 20 to surround the target body 18. The body 18 is typically surrounded by a high dielectric region fluid, such as water, filling the space 19 between the target body 18 and the dielectric shell 20. Dielectric shell or housing 20 is preferred to be a clear plastic tube. The plastic tube 20 can be cylindrical, elliptical, oval shaped, made by two circular arcs, or in a form of several flat sections such as an octagon or pentagon. Usually a bolus formed by a closed flexible plastic bladder, not shown, is positioned in the housing 20 around target body 18 to easily hold and contain the high dielectric fluid in the high dielectric region fluid area 19. FIG. 2 also shows the four variable reflective phase termination devices 15 as shown in FIG. 1.

Figure 3:
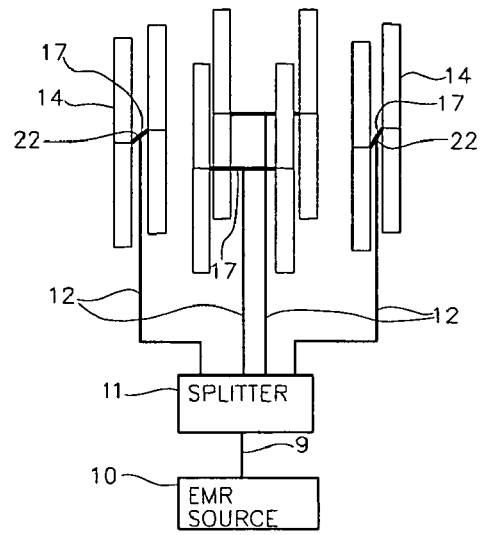
FIG. 3 is a diagram similar to that of FIG. 1, but showing a phased array system with no phase steering capability using a single electromagnetic energy source and power splitter that would provide only a central region of heating within the targeted tissue.
Figure 4:
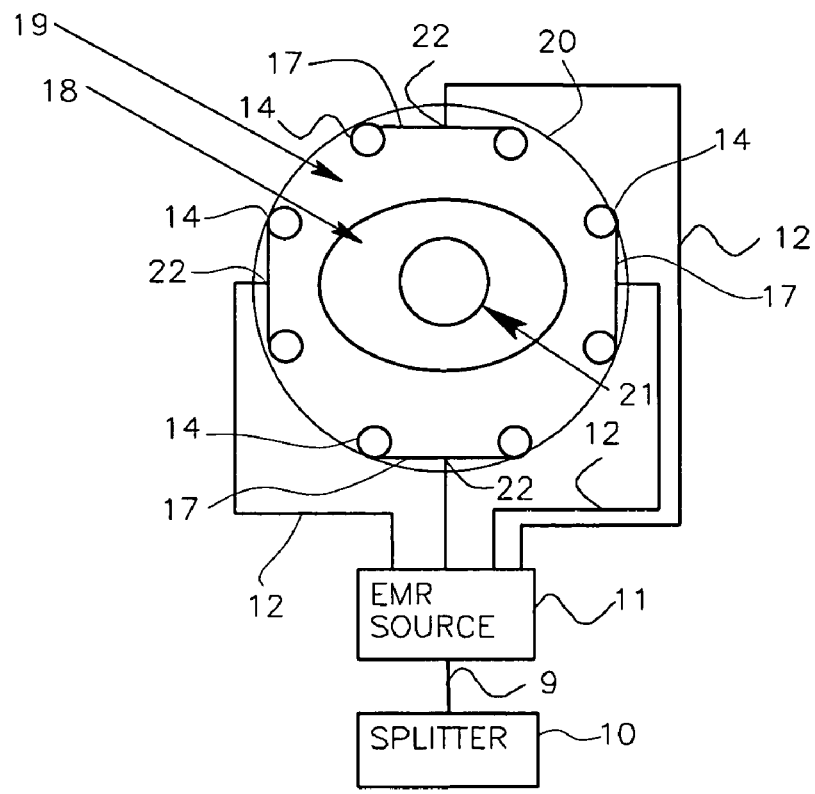
FIG. 4 is a schematic top view of the system of FIG. 3 showing an elliptical target body centrally located inside a cylindrical housing and antenna array and showing the centrally located heated area in the body.

FIGS. 3 and 4 are the same as described in the details of FIGS. 1 and 2, but with no variable reflective termination devices 15 of FIGS. 1 and 2. In this arrangement, equal phase is provided at all feed points 22. This arrangement without any variable reflective termination devices 15 has no heating region steering capability and provides only a central heating region for the apparatus as shown by central heating region 21 in body 18 in FIG. 4. This represents and is equivalent to setting all of the variable reflective phase termination devices 15 in FIGS. 1 and 2 to provide the same or equal phase at all feed points 22. Such would be the case, for example, if all four variable reflective termination devices 15 in FIGS. 1 and 2 are set to provide an equivalent open circuit at all feed points 22.

FIG. 4 is a top view of the arrangement of FIG. 3 that shows a diagrammatic cross-sectional view of the elliptical section 18 representing the human body. Again, the body is typically surrounded by a high dielectric region fluid, such as water, filling the space 19 between the body 18 and the dielectric shell 20, that is preferred to be a clear plastic tube. The plastic tube 20 can be cylindrical, elliptical, oval shaped, made by two circular arcs, or in a form of several flat sections such as an octagon or pentagon. FIG. 4 shows the central heating region 21 in body 18 that is produced when equal phases are provided to all applicator feed points 22.

FIGS. 5 and 6 are the same as described in the details of FIGS. 1 and 2, but with only one of the variable reflective termination devices 15 of FIG. 1. In this arrangement, equal phase is provided at the three feed points 22 without the variable reflective termination devices. The phase at the feed point 22 having the variable reflective termination device connected thereto can be adjusted to provide a different phase from the phase at the other three feed points. This provides steering capability, and when the variable reflective termination device 15 is set to provide a different phase from the phase at the other three feed points, provides a displaced heating region 23, FIG. 6, for the apparatus. These Figures are equivalent to FIGS. 1 and 2 having three of the variable reflective termination devices 15 set to provide the same phase to three of the feed points 22 and one of the variable reflective termination devices 15 set differently to provide a different phase to the fourth feed point. For example, one of the termination devices in FIGS. 1 and 2 can be set to provide a short circuit at the connected feed point 22 and the remaining termination devices all set to provide an open circuit to the remaining feed points 22.

FIG. 6 is a top view similar to that of FIG. 4, but shows the arrangement of FIG. 5. The heating zone or region 23 represents the approximate heating zone that would result from the variable termination device 15 being adjusted to provide an equivalent short circuit at the attached feed point 22 while the remaining feed points 22 are all provided an equivalent open circuit.

FIGS. 9 and 10 are similar to FIGS. 5 and 6 showing only one of the variable reflective termination devices of FIG. 1, but showing the variable reflective termination device connected to a different feed point 22 than shown in FIGS. 5 and 6. In this arrangement, as in the arrangement of FIGS. 5 and 6, equal phase is provided at the three feed points 22 without the variable reflective termination devices. The phase at the feed point 22 having the variable reflective termination device connected thereto can be adjusted to provide a different phase from the other three feed points. This also provides a displaced heating region 24, FIG. 10, for the apparatus, but the displacement is rotated about ninety degrees from the displacement provided by the arrangement of FIGS. 5 and 6 (compare the position of region 24 in FIG. 10 with the position of region 23 in FIG. 6). These Figures are equivalent to FIGS. 1 and 2 having three of the variable reflective termination devices 15 set the same to provide the same phase to three of the feed points 22 and one of the variable reflective termination devices set differently to provide a different phase to the fourth feed point. For example, one of the variable reflective termination device 15 of FIGS. 1 and 2 can be adjusted to provide a short circuit at the connected feed point 22 and the remaining termination devices all set to provide an open circuit to the remaining feed points 22. The comparison of the location of the heating region as steered by the arrangement of FIGS. 9 and 10 and FIGS. 5 and 6 show that with the arrangement of FIGS. 1 and 2 where three of the variable reflective termination devices provide open circuit terminations and one of the variable reflective termination devices provides a short circuit termination, the heating region is displaced away from the short circuit termination. Thus, with the arrangement of FIGS. 1 and 2, the heating region can be steered into one of four offset positions depending upon which of the four variable reflective termination devices is set to provide a short circuit termination while the other three variable reflective termination devices are set to provide open circuit terminations.

FIGS. 7 and 8 are the same as described in the details of FIGS. 1 and 2, but with only two of the adjacent variable reflective termination devices 15 of FIGS. 1 and 2. In this arrangement, equal phase is provided at the two adjacent feed points 22 without the variable reflective termination devices. The adjacent feed points 22 connected to the variable reflective termination devices 15 can be adjusted to provide different phases. This provides steering to displace the heating region. If both variable reflective termination devices 15 in FIGS. 7 and 8 are adjusted to provide a different phase than that provided to the feed points without the variable reflective termination devices to both feed points to which they are connected, the heating region 25, FIG. 8, is displaced from both applicators having the variable reflective termination devices 15 coupled thereto. This provides a displaced heating region 25 in body 18 that is rotated approximately forty five degrees in orientation from the position shown in FIG. 6. FIGS. 7 and 8 are equivalent to FIGS. 1 and 2 having two adjacent variable reflective termination devices set the same to provide the same phase to two of the adjacent feed points 22 and the other two adjacent variable reflective termination devices set differently to provide a different phase or different phases to the other two adjacent feed points. For example, two adjacent variable reflective termination devices can be set to provide an equivalent open circuit at the connected feed points 22 and the remaining two adjacent variable reflective termination devices can be set to provide an equivalent short circuit to the remaining two adjacent feed points 22. This arrangement would provide the same displaced heating region 25 in body 18 shown in FIG. 8 that is rotated approximately forty five degrees in orientation from that shown in FIG. 6. The particular adjacent pairs of applicators in the system of FIGS. 1 and 2 provided with the open circuit terminations and those provided with the short circuit terminations determine in which of four directions the heating region is displaced or offset.

It should be realized that with the arrangement of FIGS. 7 and 8, if one of the variable reflective termination devices 15 shown is adjusted to provide a termination at its connection point the same as at the connection points without the variable reflective termination devices (three connection points provide the same phase signals) and only one of the variable reflective termination devices is adjusted to provide a different termination and thus provide a different phase signal at that one connection point, the system of FIGS. 7 and 8 become equivalent to the system of either FIGS. 5 and 6 or FIGS. 9 and 10. Therefore, if only one of the variable reflective termination devices 15 shown, for example, the variable reflective termination device 15 at the top right in FIG. 8, is set to provide a different phase, e.g., that variable reflective termination device is set to provide a short circuit at its connection point 22, while the other variable reflective termination device and the two connection points without variable reflective termination devices provide open circuit terminations, the apparatus of FIGS. 7 and 8 become equivalent to the apparatus of FIGS. 5 and 6 and the deflection of the heating region is as shown in FIG. 6. Similarly, if the variable reflective termination device 15 shown in the lower left hand portion of FIG. 8 is set to provide a different phase, e.g., that variable reflective termination device is set to provide a short circuit at its connection point 22 while the other variable reflective termination device and the two connection points without variable reflective termination devices provide open circuit terminations, the apparatus of FIGS. 7 and 8 become equivalent to the apparatus of FIGS. 9 and 10 and the deflection of the heating region is as shown in FIG. 10. Further, if both variable reflective termination devices are set to provide the same termination and same phase signal as the two connections without the variable reflective termination devices so that all applicator connections provide open circuit terminations, the system of FIGS. 7 and 8 becomes equivalent to the system of FIGS. 3 and 4 with the heating region centered in the target body. Thus, with the apparatus of FIGS. 7 and 8, variable steering is provided by varying the condition of the variable reflective termination devices. If both of the variable reflective termination devices provide the same phase terminations as the two applicators without the variable reflective termination devices (all four applicators have the same phase signals) the heating region is steered to the center of the target body as shown in FIG. 4. If one or the other or both of the variable reflective termination devices provides a different phase termination at its connection point from the phase provided by the two applicators not connected to variable reflective termination devices, the heating region can be easily steered to the position shown in FIG. 6, the position shown in FIG. 10, or the position shown in FIG. 8.

With the arrangement of two variable reflective termination devices as shown in FIGS. 7 and 8, and by locating the target body in a particular rotated position within the housing 20, the heated region produced by the system can be selectively positioned within the body as desired. In order to position the heated region in the body without rotational movement of the target body in the housing with respect to the two variable reflective termination devices as described, the system of FIGS. 1 and 2 with all four connection points being coupled to variable reflective termination devices is preferred. This arrangement of FIGS. 1 and 2 allows any one or more of the variable reflective termination devices to be set to provide any arrangement of terminations to steer or position the heated region produced by the system at any selected position around the target body. By proper selection of open circuit and short circuit reflective terminations provided by selected variable reflective termination devices around the body, the system can be made equivalent to any of the systems of the remaining figures to provide a central heating region or displaced heating region positioned at any selected rotated position at forty-five degree intervals around the body as described above. If the variable reflective termination devices can provide a wider range of terminations than merely open circuits and short circuits, additional steering of the heating region can be obtained. However, the simple open and short circuit connections provide a system that is simple to operate and provides a good selection of steered heating regions.

FIGS. 11 and 12 are diagrams similar to FIGS. 5 and 6, but show the use of a parasitic applicator which reflects EMR energy back to the target. The parasitic applicator is not connected to the splitter 11 or EMR source 10, however, it is connected to a variable reflective termination device 15. The approximate position of the resulting heating pattern 26 from this arrangement with a single applicator that contains parasitic antennas is shown in FIG. 12 and is similar to that produced by the connection pattern of FIGS. 5 and 6.

FIGS. 13 and 14 are diagrams similar to FIGS. 7 and 8, but showing the use of two adjacent parasitic applicators which reflect EMR energy back to the target. The parasitic applicators are not connected to the power splitter or the EMR source 10, however, they are each connected to a variable reflective termination device 15. The approximate position of the resulting heating pattern 27 from this arrangement with two adjacent applicators each containing parasitic antennae is shown in FIG. 14 and is similar to that produced by the connection pattern of FIG. 8.

FIGS. 15 and 16 are diagrams similar to FIGS. 11 and 12, showing the use of a parasitic applicator which reflects EMR energy back to the target. The parasitic applicator is not connected to the splitter 11 or EMR source 10, however, it is connected to a variable reflective termination device 15. However, the parasitic applicator with coupled variable reflective termination device 15 in FIGS. 15 and 16 is at a different location than in FIGS. 11 and 12. The approximate position of the resulting heating pattern 28 from this arrangement with a single applicator that contains parasitic antennas is shown in FIG. 16 and is similar to that produced by the connection pattern of both FIGS. 11 and 12 and FIGS. 9 and 10.

FIGS. 11 to 16 show that it is not necessary to have a direct connection of all applicators to the power source. Parasitic applicators will reflect EMR energy and can provide steering capability to the system. A minimum system with parasitic applicators to provide phase array steering would be one primary applicator and one parasitic applicator with the parasitic applicator having a variable reflective termination device to adjust the phase of the reflected radiation from the parasitic applicator. Above that, any selected number of primary and parasitic applicators could be used. In addition, combinations of primary and parasitic applicators could be used. An example of such a combination would be a single primary dipole or monopole antenna device that has reflective parasitic antennas to each side of the driven or primary antenna where the side antennas would act as parasitic reflectors based upon their termination. This could even be single dipoles or monopoles having metal strip reflectors to the two sides to form the actual antenna set and the feed point of the dipole or monopole type antenna could have the variable reflective termination device.

FIG. 17 shows an arrangement of the invention where the applicator comprises two cylindrical metal rings 14 which extend around the housing 20 to enclose the target and a bolus containing a dielectric fluid, such as water, between the target and the housing walls. A four channel feed system for coupling EMR power to the applicator provides four energy supply connection points 22 spaced at ninety degree intervals around the rings to provide a balanced feed to the rings. The rings form a single dipole ring applicator. The energy supply connection points 22 are shown as coaxial cables 12 connected to respective rings. Variable phase termination devices 15 for some or all of the energy supply connection points 22 enable the same heating pattern steering that has been shown by the other figures. The connections of the variable reflective termination devices can be placed at each of the energy supply connection points and connected to the coaxial cable connections, as shown, can be connected to some of the energy supply connection points, or can be connected to respective rings between the energy supply connection points at other positions around the applicator. Further, more than four variable reflective termination devices could be used. The termination devices could include coaxial cables connected to the respective rings 14 or to the coaxial cables 12 at the energy supply connection points 22, direct connections between the respective rings, or could be inserts inserted into the space between the respective rings to create short circuits or other terminations.

While the two cylindrical metal rings of FIG. 17 may be considered or referred to as forming a single applicator, since the radiation provided or reflected from different locations around the circumference of the rings can vary and can be controlled, for purposes of the invention, such an applicator is considered as a plurality of applicators.

It should be realized that with any of the applicators, various termination means can be used as the variable reflective termination devices. These can be manually operated devices to provide short circuit, open circuit, or other connections, such as manually operated mechanical switches or lengths of coaxial cable manually connected to a coaxial cable connector at the feed points, or can be remotely controlled terminations such as controlled by electric coaxial relays, PIN diode termination switches, or other remotely controlled switches or devices. Further, the termination can be adjusted by using variable capacitance or other devices, or can be adjusted by adjusting cable lengths coupling a reflective termination device to the feed point. All of these as well as other means of creating reflective terminations at the energy supply connection points or other termination points are considered as variable reflective termination devices within the scope of the invention.

The electromagnetic radiation used with the invention should be in the form of radio frequency and microwave energy in order to create the desired heating regions in the target body.

The applicators can use various antenna configurations such as dipoles, folded dipoles, monopoles, waveguides, parallel strip horns, microcircuit patch antennas, two concentric metal cylinders, etc. These antenna radiators provide a dominant linear polarization and are suitable for providing the deep heating that would be centralized when such deep heating is desired. Circularly polarized antennae such as spiral antenna radiators can also be used. However, circular polarization would not provide as much central heating from an array as a result of the overlapping EMR fields when more than two are used. This is because the dominant fields of spirals that are overlapping from varying directions will not be co-aligned. It is still possible to use such spiral antennas with variable reflective terminations and as parasitic antenna, but the effects on the heating pattern from such will be different than for the linearly polarized antenna arrays.

While the arrangements of the embodiments of FIGS. 5-16 can be used for systems which provide limited steering as described for each embodiment, the embodiment of FIGS. 1 and 2 provides a full range of steering capability and is thus the preferred system to provide maximum steering capability and flexibility to a user of the system. However, while the embodiment of FIGS. 1 and 2 shows all applicators directly coupled to the EMR energy source, this direct coupling is not necessary for the full range of steering and flexibility. A system with the full range of steering can include parasitic applicators or combinations of primary and parasitic applicators. The important thing to get the full range of steering is to provide a variable reflective termination device coupled to each applicator in the system.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow:

What is claimed is:

1. Apparatus for irradiating a target with electromagnetic radiation to produce a heated region in a selected position in the target, comprising:
   a plurality of energy radiator applicators having an energy supply connection point;
   an electromagnetic energy source;
   means coupling the electromagnetic energy source to the energy supply connection point of at least one of the plurality of energy radiator applicators to supply electromagnetic energy from the energy source to the coupled connection point;
   at least one variable reflective termination device coupled to the energy supply connection point of at least one of the plurality of energy radiator applicators;
   wherein the variable reflective termination device can be adjusted to adjust the reflective phase at the energy supply connection point to which it is coupled to adjust the region within the target in which the radiated electromagnetic energy is intensified thereby selecting the position of the heated region in the target.

2. Apparatus for irradiating a target with electromagnetic radiation to produce a heated region in a selected position in the target, according to claim 1, wherein the means coupling the electromagnetic energy source to the energy supply connection point of at least one of the plurality of energy radiator applicators couples the electromagnetic energy source to the energy supply connection point of a plurality of energy radiator applicators.

3. Apparatus for irradiating a target with electromagnetic radiation to produce a heated region in a selected position in the target, according to claim 2, wherein the means coupling the electromagnetic energy source to the energy supply connection point of a plurality of energy radiator applicators includes an electromagnetic energy power splitter to split the electromagnetic energy from the electromagnetic energy power source among the plurality of coupled energy radiator applicators.

4. Apparatus for irradiating a target with electromagnetic radiation to produce a heated region in a selected position in the target, according to claim 3, wherein the at least one variable reflective termination device coupled to the energy supply connection point of at least one of the plurality of energy radiator applicators includes a cable coupling the variable reflective termination device to the at least one of the plurality of energy radiator applicators.

5. Apparatus for irradiating a target with electromagnetic radiation to produce a heated region in a selected position in the target, according to claim 4, wherein the at least one variable reflective termination device is variable by a user between an open circuit state and a short circuit state.

6. Apparatus for irradiating a target with electromagnetic radiation to produce a heated region in a selected position in the target, according to claim 5, wherein the reflective phase at the energy supply connection point to which the variable reflective termination device is coupled is determined by the state of a coaxial cable termination and the length of the cable between the coaxial cable termination and the energy supply connection point.

7. Apparatus for irradiating a target with electromagnetic radiation to produce a heated region in a selected position in the target, according to claim 6, wherein the electromagnetic energy provided to the coupled connection point has a predetermined wavelength, and wherein the length of the cable coupling to the central energy supply connection point is a predetermined fraction of the predetermined wavelength of the electromagnetic energy.

8. Apparatus for irradiating a target with electromagnetic radiation to produce a heated region in a selected position in the target, according to claim 7, wherein the at least one variable reflective termination device coupled to the energy supply connection point of at least one of the plurality of energy radiator applicators is more than one variable reflective termination device each of the more than one variable reflective termination device being coupled to the energy supply connection point of one of the plurality of energy radiator applicators.

9. Apparatus for irradiating a target with electromagnetic radiation to produce a heated region in a selected position in the target, according to claim 8, wherein the apparatus further includes a housing in which a target to be irradiated is adapted to be located and the plurality of energy radiator applicators are spaced around the housing.

10. Apparatus for irradiating a target with electromagnetic radiation to produce a heated region in a selected position in the target, according to claim 9, additionally including a dielectric fluid having an impedance approximately equivalent to an applicator impedance at the predetermined wavelength filling the housing adapted to be around the target.

11. Apparatus for irradiating a target with electromagnetic radiation to produce a heated region in a selected position in the target, according to claim 10, wherein the target is a living body.

12. Apparatus for irradiating a target with electromagnetic radiation to produce a heated region in a selected position in the target, according to claim 11, wherein each of the plurality of energy radiator applicators includes at least one linear antenna.

13. Apparatus for irradiating a target with electromagnetic radiation to produce a heated region in a selected position in the target, according to claim 12, wherein the at least one linear antenna in each of the plurality of energy radiater applicators is a dipole antenna.

14. Apparatus for irradiating a target with electromagnetic radiation to produce a heated region in a selected position in the target, according to claim 12, wherein at least one of the energy radiator applicators is a parasitic applicator not coupled directly to the electromagnetic energy source.

15. Apparatus for irradiating a target with electromagnetic radiation to produce a heated region in a selected position in the target, according to claim 14, wherein a variable reflective termination device is coupled to the parasitic energy radiator applicator.

16. Apparatus for irradiating a target with electromagnetic radiation to produce a heated region in a selected position in the target, according to claim 11, wherein the plurality of energy radiator applicators is four energy radiator applicators.

17. Apparatus for irradiating a target with electromagnetic radiation to produce a heated region in a selected position in the target, according to claim 16, wherein the electromagnetic energy power splitter is coupled to the four energy radiator applicators and splits the electromagnetic energy from the electromagnetic energy power source among the four energy radiator applicators.

18. Apparatus for irradiating a target with electromagnetic radiation to produce a heated region in a selected position in the target, according to claim 17, wherein the more than one variable reflective termination devices is four variable reflective termination devices with one of the four variable reflective termination devices coupled to the energy supply connection point of a different one of each of the four energy radiator applicators.

19. Apparatus for irradiating a target with electromagnetic radiation to produce a heated region in a selected position in the target, according to claim 11, wherein the plurality of energy radiator applicators is an applicator comprising a pair of rings adapted to be encircle the target and coupled to the electromagnetic energy source and the at least one variable reflective termination device so that energy can be radiated differently from different locations around the rings thereby effectively providing a plurality of energy radiator applicators.

20. Apparatus for irradiating a target with electromagnetic radiation to produce a heated region in a selected position in the target, comprising:
   a plurality of energy radiator applicators, each applicator including at least one antenna, and having an energy supply connection point;
   an electromagnetic energy source;
   means coupling the electromagnetic energy source to the energy supply connection point of each of the energy radiator applicators to supply electromagnetic energy from the energy source to the coupled connection points;
   at least one variable reflective termination device coupled to the energy supply connection point of at least one of the plurality of energy radiator applicators;
   wherein the variable reflective termination device can be adjusted to adjust the reflective phase at the energy supply connection point to which it is coupled to adjust the region within the target in which the radiated electromagnetic energy is intensified thereby selecting the position of the heated region in the target.

21. A method for irradiating a target with electromagnetic radiation to produce a heated region in a selected position in the target, comprising the steps of:
   arranging a plurality of energy radiator applicators having an energy supply connection point around a target to be irradiated;
   supplying electromagnetic energy from an electromagnetic energy source to the energy supply connection point of at least one of the plurality of energy radiators;
   connecting at least one variable reflective termination device to the energy supply connection point of at least one of the plurality of energy radiator applicators; and
   adjusting the at least one variable reflective termination device to adjust the reflective phase at the energy supply connection point to which it is coupled to steer the region within the target in which the radiated electromagnetic energy is intensified to thereby steer the heated region in the target to a selected position.

* * * * *